United States Patent [19]
Keinan

[11] Patent Number: 5,496,854
[45] Date of Patent: Mar. 5, 1996

[54] METALLOCENES AS ANTI-TUMOR DRUGS

[75] Inventor: Ehud Keinan, 6549 Dennison Ave., San Diego, Calif. 92122

[73] Assignees: Technion Research & Development Foundation Ltd., Haifa, Israel; Ehud Keinan, San Diego, Calif.; a part interest

[21] Appl. No.: 387,785

[22] PCT Filed: Aug. 19, 1993

[86] PCT No.: PCT/US93/07875

§ 371 Date: Feb. 17, 1995

§ 102(e) Date: Feb. 17, 1995

[87] PCT Pub. No.: WO94/04142

PCT Pub. Date: Mar. 3, 1994

[30] Foreign Application Priority Data

Aug. 19, 1992 [IL] Israel .................................. 102866

[51] Int. Cl.$^6$ .................. A61K 31/28; C07F 17/00; C07F 7/28
[52] U.S. Cl. .................. 514/492; 556/53; 556/54; 556/55; 556/56
[58] Field of Search .................. 556/53, 54, 55, 556/56; 514/492

[56] References Cited

U.S. PATENT DOCUMENTS 5,002,969 3/1991 Köpf-Maier et al. .................. 514/492

OTHER PUBLICATIONS

Kon, L. Y. et al., J. Am. Chem. Soc., vol. 113, pp. 9027 (1991).

Murthy M. S. et al., Proc. Am. Assoc. Cancer Res., vol. 27, pp. 279 (1986).

Andra, K., J. Organomet. Chem., vol. 11, No. 3, pp. 567–570 (1968).

Primary Examiner—Porfirio Nazario-Gonzalez
Attorney, Agent, or Firm—Cowan, Liebowitz & Latman

[57] ABSTRACT

The invention relates to novel titanocene derivatives possessing chemotherapeutic activity and method for their preparation. These compounds possess two cyclopentadiene rings linked to titanium as a central atom and bound covalently to two phenoxy groups which possess a substituent R selected from the group consisting of $COOCH_3$, $COOC_2H_5$, H, $COOCH_2CH_2OCH_2CH_2OCH_3$ and are free from amino, nitro, chloride and fluoride groups. The novel compounds represent a compromise between the main properties for an antitumor agent, i.e., electrophilicity and stability, being water soluble. Cytotoxicity measurements of these compounds showed significant growth inhibition properties, expressed in terms of $IC_{50}[M]$ values.

11 Claims, No Drawings

METALLOCENES AS ANTI-TUMOR DRUGS

This application is a request for U.S. examination under 35 U.S.C. §371 of International application No. PCT/US93/07875, filed Aug. 19, 1993.

The present invention relates to new titanocene compounds. More particularly the invention relates to new titanocene complexes and methods for their preparation, which possess chemotherapeutic activity being useful for the treatment of human tumors.

BACKGROUND OF THE INVENTION

There are known metallocene complexes containing titanium, vanadium, niobium and molibdenum as a metal ion, which are active against a variety of tumor cell lines such as B16 melanoma, colon 38 carcinoma, Lewis lung carcinoma, etc. It has been shown that the activity of vanadium complexes related to the formula $Cp_2VCl_2$ where $C_p$ is cyclopentadiene, against human epidermoid (HEP-2) tumor cells in vitro and against mouse tumor cells, is similar to that of cis-platin (Murthy M. S. et el. Proc. Am. Assoc. Cancer Res. 1986, 27, 279). A study which was carried out with a corresponding molibdenum compound, supports the possibility that these complexes are binding 5'-phosphate terminated polynucleotides, thus inhibiting DNA replication, by a mechanism which different from that of cis-platinum complexes (Kon, L. Y. et al. J. Am. Chem. Soc. 1991, 113, 9027).

Titanocene dichloride, one of the first metallocene compounds which was tested, was found to be indeed a very reactive anti-tumor reagent. Due to its rapid hydrolysis to the corresponding dihydroxy derivative, it is quite reasonable to assume that this dihydroxy titanocene is the actual drug. Accordingly, many references can be found describing titanocene compounds which were tested in an attempt to possess an improved cytotoxity. Examples of such compounds include halides, pseudohalides, carboxylates, and phenolates. However, no significant improvement over titanocene dichloride in the antitumor activity has been achieved.

The metallocene diacido complexes, having the general formula $(C_5H_5)_2MX_2$ are characterized by the following structural features:

The geometry of the complexes is that of a distorted tetrahedron.

The complexes contain two uninegative acido ligands X coordinated to the central metal atom and arranged in adjacent "cis-like" position.

The sites of the other two ligands are occupied by two anionic cyclopentadienyl rings.

Attempts to modify the cyclopentadienide rings lead to a decreased biological activity.

In a very recent U.S. Pat. No. 5,002,969 there are described cytostatic pharmaceutical compositions based on titanocene complexes. A group which is present in all these complexes is an amino or substituted amino bound to the titanoceno moiety. These compounds are obtained by a reaction between a titanocene dihalogenide and an amino phenol, lithium aminophenolate, or lithium amino thiophenolate. There is mentioned that the compounds have a better solubility in water than titanocene dichloride, fact which improves their application and dosing. Other titanocene complexes which were described, differ by their ionic character from the neutral titanocene compounds. Most of them correspond to the general formula $[(C_5H_5)_2TiXL]^+Y^-$ where X and Y are anions and L is a neutral donor molecule. These ionic titanocene complexes are characterized by their improved water solubility compared with the neutral titanocene compounds.

It is an object of the present invention to provide novel titanocene derivatives. It is another object of the present invention to provide novel titanocene derivatives which possess a superior cytotoxic activity than the cis-platinum complexes.

BRIEF DESCRIPTION OF THE INVENTION

The invention relates to novel titanocene derivatives which comprise two cyclopentadiene rings linked to titanium as a central atom, which are bound covalently to two phenoxy groups which possess a substituent R which is selected from the group consisting of: $COOCH_3$, $COOC_2H_5$, H, $COOCH_2CH_2OCH_2CH_2OCH_3$ being free from amino groups, nitro group, chloride and fluoride. The above novel titanocene derivatives represent a compromise between the two main properties required for an antitumor agent: electrophilicity and stability.

DETAILED DESCRIPTION OF THE INVENTION

It is a generally accepted assumption that titanocenes, as well as other antitumor agents, do react with DNA in a similar manner. Therefore, the two main properties required for the drugs, in addition to the water solubility, are electrophilicity and stability in order to survive the aqueous biological medium during the time required to reach the target. The inventor's approach was to synthesize the new compounds which should possess these two main properties. Accordingly, the titanocene compounds envisaged should contain groups such as phenolates, having the role of moderate leaving groups, and appropriate substituents on the phenyl rings which impart stability to these compounds. Thus, considering the electrophilic role played by the metallocene drug in binding to the nucleophilic sites of polynucleotides, it may be concluded that an optimal biological activity would be achieved when the titanocene compounds, according to the present invention, will contain leaving groups of moderate reactivity, such as phenols substituted at their 4-position with $COOCH_3$, $CO_2CH_2CH_2CH_2OCH_2CH_2OCH_3$, $CH_2$–$CH_3$, $COCH_3$, H and of course possessing a satisfactory hydrolytic stability.

Typical examples of the novel titanocene derivatives are as follows:

1. Bis(4-cyanophenolato)bis($n^5$-cyclopentadienyl)titanium (IV), hereinafter referred to as TCN.
2. Bis(4-methoxycarbonylphenolato)bis($n^5$-cyclopentadienyl)titanium(IV), hereinafter referred to as TPE.
3. Bis(4-ethoxycarbonylphenolato)bis($n^5$-cyclopentadienyl) hereinafter referred to as TEE1.
4. Bis[4-(2-methoxyethoxy)ethoxy]carbonylphenolato] bis($n^5$-cyclopentadienyl)titanium(IV), hereinafter referred to as TEG.
5. Bis[4-(methoxy)ethoxycarbonylphenolato] bis($n^5$cyclopentadienyl)titanium(IV), hereinafter referred to as TMEM.
6. Bis[4-(2-dimethylamino)ethoxycarbonylphenolato] bis($n^5$-cyclopentadienyl)titanium(IV), hereinafter referred to as TCA.
7. Bis[4-(2-trimethylammono)ethoxycarbonylphenolato] bis($n^5$-cyclopentadienyl)titanium(IV), hereinafter referred to as TCE.

Cytotoxicity measurements carried out with the above compounds show significant growth inhibition properties of these compounds expressed in terms of $IC_{50}[M]$ values.

In the following Table 1 are presented the results which show that these compounds are much superior than the known titanocene dichloride (TDC) under the same conditions. The value of the ratio Ti/Pt represents the relative activity of TPE as compared with that of cis-platinum. The first four entries represent data of normal cell lines and the other ten entries represent the experiments with tumor cell lines.

TABLE 1

Cytotoxic data of titanocene derivatives.

| Cell line | Cell type | TPE | TDC | cisPt | $\frac{Ti}{Pt}$ |
| --- | --- | --- | --- | --- | --- |
| CHO | Chinese Hamstead Ovary | $1.3 \times 10^{-5}$ | $10^{-3}$ | $3.1 \times 10^{-5}$ | 2 |
| HMEC | Normal Human Mammary | $3.1 \times 10^{-6}$ | $1.3 \times 10^{-4}$ | $6.3 \times 10^{-5}$ | 20 |
| NHDF | Normal Human Skin | $1.6 \times 10^{-6}$ | $10^{-3}$ | $3.1 \times 10^{-5}$ | 20 |
| NHEK | Normal Keratino Epithelial | $3.1 \times 10^{-6}$ | $10^{-3}$ | $6.3 \times 10^{4}$ | 200 |
| Capan 1 | Pancreas Carcinoma | $3.9 \times 10^{-7}$ | $5.0 \times 10^{-4}$ | $3.9 \times 10^{-6}$ | 10 |
| HT-29 | Colon Carcinoma | $3.9 \times 10^{-4}$ | $5.0 \times 10^{-4}$ | $1.3 \times 10^{-4}$ | 200 |
| SK-Mel-28 | Melanoma | $1.6 \times 10^{-6}$ | $10^{-3}$ | $1.6 \times 10^{-5}$ | 10 |
| H-322 | Lung Carcinoma | $6.3 \times 10^{-7}$ | $10^{-3}$ | $6.3 \times 10^{-5}$ | 100 |
| UCLA-P3 | Lung Carcinoma | $3.1 \times 10^{-6}$ | $10^{-3}$ | $6.3 \times 10^{-5}$ | 20 |
| MCF-7 | Breast Cancer | $2.0 \times 10^{-6}$ | $10^{-3}$ | $1.3 \times 10^{-4}$ | 100 |
| HL-60 | B-cell Leukemia | $3.1 \times 10^{-6}$ | $10^{-3}$ | $7.8 \times 10^{-6}$ | 2 |
| Molt-4 | T-cell Leukemia | $-10^{-6}$ | $10^{-3}$ | $-10^{-5}$ | 10 |
| Ovcar-3 | Ovarian Carcinoma | $6.3 \times 10^{-6}$ | $10^{-3}$ | $6.3 \times 10^{-5}$ | 10 |
| P-388 | Mouse Leukemia | $3.9 \times 10^{-6}$ | $5.0 \times 10^{-4}$ | $9.8 \times 10^{-7}$ | 025 |

The cytotoxicity results with a number of titanocene derivatives, expressed in concentrations (M) are presented in the attached Table 2 for a number of solid tumors. For combating solid tumors, the titanocene derivatives according to the present invention may be employed as such or as pharmaceutical compositions containing at least one titanocene complex as described above in addition to pharmaceutically acceptable excipients, diluents and/or auxiliary agents. The excipient can serve as an agent for promoting absorption of the medicament by the body or as formulation auxiliary, sweetener, flavouring agent, colourant or preservative. The pharmaceutical formulations of the active compounds are preferably in the form of unit doses matched to the particular mode of administration. The amount of the active compound is chosen so that one or more units are usually sufficient for an individual therapeutic administration. In addition to that, the medicaments with the active compound, may contain also one or more other pharmacologically active constituents, such as: alkylating agents, antimetabolites antibiotics, vitamins, enzymes and heavy metal compounds. The novel titanocene derivatives, according to the present invention, can be prepared from common chemical reagents using standard equipment. It should be realized, that the Examples for their preparations presented hereinafter are only for illustration and many other routes may be conceived for their syntheses.

EXAMPLE 1

Preparation of Bis(4-cyanophenolato)bis ($n^5$-cyclopentadienyl)titanium(IV) TCN An amount of 238 mg (2 mmol) of 4-cyanophenol was dissolved in 10 ml of benzene and 200 mg of sodium hydride 80% in mineral oil (6.67 mmol) was added and stirred at room temperature for about 10 minutes. To this mixture an amount of 249 mg (1 mmol) of titanocene dichloride was added and the mixture refluxed for 8 hours, cooled to room temperature and placed on a short column containing silica gel (pre-washed with acetone). The elution with methylene chloride followed by removal of the solvent under reduced pressure, yielded crude TCN. By purifying the crude TCN on a chromatographic columns (silica gel, ethyl acetate-hexane), an amount of 290 mg of pure TCN (70% yield) was obtained in the form of a yellow solid.

The analysis of the product on $^1$H NMR (CDCl$_3$) was as follows: 7.52 (d,J=8.6 Hz,4H), 6.64(d,J=8.6 Hz, 4 Hz), 6.31(s, 10H).

EXAMPLE 2

Preparation of Bis(methoxycarbonylphenolato) bis($n^5$-cyclopentadienyl)titanium(IV) TPE In the same manner as in Example 1, an amount of 273 mg (2 mmol) of methyl 4-hydroxybenzoate was reacted with 249 mg (1 mmol) of titanocene dichloride. An amount of 364 mg of TPE (81% yield) in the form of a yellow solid was obtained.

The analysis of the product on $^1$H NMR (CDCl$_3$) was as follows: 7.91 (d,J=8.7 Hz, 4H),6.64 (d,J=8.7 Hz, 4H), 6.33 (s,10H), 2.56 (s, 6H).

EXAMPLE 3

Preparation of Bis(4-ethoxycarbonylphenolato)bis ($n^5$-cyclopentadienyl)titanium(IV) TEE1.

In the same manner as in Example 1, an amount of 332 mg (2 mmol) of ethyl 4-hydroxybenzoate was reacted with 249 mg (1 mmol) of titanocene dichloride. An amount of 417 mg of TEE1 (81% yield) was obtained.

The analysis of the product on $^1$H NMR (CDCl$_3$) was as follows: 7.90 (d, J=8.6 Hz, 4H), 6.61 (d, J=8.6 Hz, 4H), 6.31 (s, 10H), 2.94 (q, J=7.3 Hz, 4H), 1.21 (t, J=7.3 Hz, 6H).

EXAMPLE 4

Preparation of Bis[4-(2-(2-methoxyethoxy)ethoxy] carbonylphenolato]bis(n$^5$ -cyclopentadienyl)titanium(IV) TEG (a) In a first step, an amount of 1 g (43 mmol) of sodium was dissolved in 25 of ml 2-(2-methoxyethoxy)ethanol. To the resulted solution an amount of 3 g (22 mmol) of methyl 4-hydroxybenzoate was added and the mixture was heated to 130° C. for 24 hours; after cooling to room temperature, it was acidified with a hydrochloric acid solution (3N) and extracted with ethyl acetate. The removal of the solvent under reduced pressure and column chromatography of the residue (silica gel, hexane:ethyl acetate 3:1) afforded 2-(2-methoxyethoxy)ethyl 4-hydroxybenzoate, in the form of a colourless oil in essentially quantitative yield.

(b) In the second step, an amount of 480 mg (2 mmol) of the product obtained in step (a), was reacted with 249 mg (1 mmol) of titanocene dichloride, as described in Example 1. An amount of 355 mg of TEG (54% yield) was obtained.

The analysis of the product on $^1$H NMR (CDCl$_3$) was as follows: 7.95 (d, J=8.6 Hz, 4H), 6.60 (d, J=8.6 Hz, 4H) 6.31 (s, 10H), 4.45 (t, J=5.0 Hz, 4H), 3.83 (t,J=5.0 Hz, 4H), 3,70 (t, J=4.6 Hz, 4H), 3.57 (t, J=4.6 Hz, 4H), 3.38(s, 6H).

EXAMPLE 5

Preparation of Bis[4-(2-methoxy)ethoxycarbonylphenolato]bis(n$^5$ -cyclopentadienyl)titanium(IV) TMEM (a) In the first step (as in the Example 4) 1 g (43 mmol) of sodium was dissolved in 25 ml of 2-methoxyethanol. An amount of 3.0 g (22 mmol) of methyl 4-hydroxy-benzoate was added, producing 2-methoxyethyl 4-hydroxybenzoate, as a colourless oil, in essentially quantitative yield.

(b) In the second step, an amount of 392 mg (2 mmol) of the product obtained in step (a) was reacted with 249 mg (1.1 mmol) of titanocene dichloride as described above in Example 1, affording 330 mg of TMEM (58% yield).

The analysis of the product on $^1$H NMR (CDCl$_3$) was as follows: 7.96 (d, J=8.6 Hz, 4H), 6.60 (d, J=8.6 Hz, 4H), 4H), 6.29 (s, 10H), 4.42 (t, J=4.8 Hz, 4H), 3.70 (t, J=4.8 Hz, 4H), 3.70 (t, J=4.8 Hz, 4H), 3.40 (s, 6H).

EXAMPLE 6

Preparation of Bis[4-(2-dimethylamino)ethoxycarbonylphenolato]bis (n$^5$-cyclopentadienyl) titanium(IV) TCA (a) In a first step, 1 g (43 mmol) of sodium was dissolved in 20 ml of 2-(dimethylamino)ethanol. An amount of 3.0 g (22 mmol) of methyl 4-hydroxybenzoate was added and heated to 110° C. for 24 hours and then cooled to room temperature. The solvent was removed under reduced pressure and using a column chromatography (silica gel, chloroform-methanol), a white solid of 2-(dimethylamino)-ethyl 4-hydroxybenzoate was obtained.

(b) In the second step, an amount of 418 mg (2 mmol) of the product obtained in step (a) was reacted with 249 mg (1 mmol) of titanocene dichloride, as described in Example 1, affording 330 mg of TCA (58% yield).

The analysis of the product on $^1$H NMR (CDCl$_3$) was as follows: 7.94 (d,J=8.6 Hz, 4H), 6.59 (d, J=8.6 Hz, 4H), 6.30 (s, 10H), 4.39 (t, J=7.2 Hz, 4H), 2.71 (t, J=7.2 Hz, 4H), 2.34 (s, 12H).

EXAMPLE 7

Preparation of Bis[4-(2-trimethylamino)ethoxy-carbonylphenolato]bis (n$^5$-cyclopentadienyl) titanium(IV)

The TCA product as obtained in the previous Example 6, was treated with an excess of methyl iodide (10 equiv) in benzene for about 6 hours. A yellow solid of TCE is formed, collected by filtration, washed by benzene and ether and dried.

The analysis of the product on $^1$H NMR (DMSO) was as follows: 7.87 (d, J=8.6 Hz, 4H), 6.66 (d, J=8.6 Hz, 4H), 6.44 (s, 10H), 4.64 (m, 4H), 3.77 (m, 4H), 3.18 (s, 18H).

TABLE 2

| | Column 1 | Column 2 | cis-platin | TEG | TMEM | TEE-1 | TCE | TPE | TP |
|---|---|---|---|---|---|---|---|---|---|
| 1 | CHOChin. Harm. Ov. | | −4.51 | | −4.30 | −4.60 | | −4.80 | −4.20 |
| 2 | HMEC | Nor. Hum. | −4.20 | | −4.60 | −6.11 | | −5.70 | −3.89 |
| 3 | NHDF | Nor. Humn Skin | −4.51 | | −4.30 | −4.89 | | −5.41 | −4.51 |
| 4 | Capan-1 | Pan (a) | −5.41 | | −4.89 | −5.51 | −4.00 | −6.41 | −4.20 |
| 5 | HT-29 | Colon car. | −3.89 | | −4.60 | −5.20 | −4.00 | −5.41 | −4.20 |
| 6 | SK ML-28 | Melanoam | −4.80 | | −4.60 | −5.51 | | −5.41 | −3.89 |
| 7 | H-322 | Lnng Car. | −4.20 | | −4.89 | −5.80 | −4.00 | −6.20 | −4.20 |
| 8 | UCLA-P3 | Lung Car. | −4.20 | | | −5.20 | | −5.51 | −3.89 |
| 9 | MCF-7 | Mamary Car. | −3.89 | | −4.89 | −5.80 | −4.30 | −5.70 | −4.20 |
| 10 | HL-60 | Leukemia | −5.11 | | −4.60 | −5.51 | | −5.70 | −3.30 |
| 11 | Molt-4 | Leukemia | −5.00 | −4.00 | −7.00 | −7.00 | −4.00 | −6.00 | −4.00 |
| 12 | P-388 | Mouse | −6.01 | | | −4.89 | | −5.41 | −4.20 |
| 13 | NHEK | Normal | −3.20 | | | −5.80 | | −5.51 | |
| 14 | Ovar-3 | Ovarian car. | −4.20 | −4.00 | −4.60 | −5.20 | −4.00 | −5.20 | −3.89 |

TABLE 2-continued

| | Column 1 | Column 2 | cis-platin | TEG | TMEM | TEE-1 | TCE | TPE | TP |
|---|---|---|---|---|---|---|---|---|---|
| 15 | SIHA | Cerv. Carc. | | | −4.60 | | −4.00 | | |
| 16 | MCF-7 (Adr) | Adri (b) | | | −5.51 | | | | |
| 1 | −3.00 | −3.00 | −3.00 | −3.00 | | −4.00 | −4.60 | −3.00 | −4.30 |
| 2 | −3.30 | −3.00 | −3.00 | −3.00 | | −4.60 | −5.20 | −3.89 | −4.00 |
| 3 | −3.30 | −3.00 | −3.00 | −3.00 | | −4.00 | −4.00 | −3.00 | −4.00 |
| 4 | −3.60 | −3.00 | −3.00 | −3.00 | | −4.30 | −5.51 | −3.30 | −4.30 |
| 5 | −3.60 | −3.30 | −3.30 | −3.00 | | −4.00 | −4.89 | −3.30 | −4.30 |
| 6 | −3.30 | −3.00 | −3.00 | −3.00 | | −4.60 | −5.51 | −3.00 | −4.00 |
| 7 | −3.30 | −3.00 | −3.00 | −3.00 | −4.00 | −4.30 | −4.30 | −3.00 | −4.30 |
| 8 | −3.60 | −3.00 | −3.00 | −3.00 | −4.30 | | | −3.00 | |
| 9 | −3.30 | −3.00 | −3.00 | −3.00 | −4.30 | −4.89 | −4.89 | −3.00 | −4.30 |
| 10 | −3.00 | −3.60 | −3.00 | −3.00 | −4.00 | −4.00 | −5.80 | −3.00 | −4.00 |
| 11 | −2.00 | −3.00 | −3.00 | −3.00 | | −4.00 | −4.00 | −3.00 | −4.00 |
| 12 | −3.60 | −3.00 | −3.00 | −3.00 | −5.00 | | | −3.30 | |
| 13 | | | | | | | | −3.00 | |
| 14 | −3.60 | −3.00 | −3.00 | −3.00 | | −4.30 | −5.51 | −3.00 | −4.00 |
| 15 | | | | | | −4.30 | −4.30 | | −4.30 |
| 16 | | | | | | | | | |

(a) Pancrease Car.
(b) Adriyamicin.

I claim:

1. Novel titanocene derivatives which comprise two cyclopentadiene rings linked to titanium as a central atom, which are bound covalently to two phenoxy groups which possess a radical substituent R which is selected from the group consisting of:

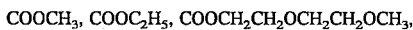

$COOCH_3$, $COOC_2H_5$, $COOCH_2CH_2OCH_2CH_2OCH_3$, being free from amino group, nitro group, chloride and fluoride.

2. Bis(4-cyanophenolato)bis($n^5$-cyclopentadienyl)titanium (IV).

3. Bis(4-methoxycarbonylphenolato)bis($n^5$-cyclopentadienyl)titanium(IV).

4. Bis(4-ethoxycarbonylphenolato)bis($n^5$-cyclopentadienyl)titanium(IV).

5. Bis(4-[2-(methoxyethoxy)ethoxy]carbonylphenolato-)bis($n^5$-cyclopentadienyl)titanium(IV).

6. Bis[4-(2-methoxy)ethoxycarbonylphenolato]bis($n^5$-cyclopentadienyl)titanium(IV).

7. Bis[4-(2-dimethylamino)ethoxycarbonylphenolato]bis($n^5$-cyclopentadienyl)titanium(IV).

8. Bis[4-(2-trimethylamino)ethoxycarbonylphenolato]bis($n^5$-cyclopentadienyl)titanium(IV).

9. A method of treating tumors in a patient, which comprises administering to the patient an effective amount of a titanocene derivative comprising two cyclopentadiene rings linked to titanium as a central atom, which are bound covalently to two phenoxy groups which possess a radical substituent R selected from the group consisting of H, $COOCH_3$, $COOCH_2H_5$, and $COOCH_2CH_2OCH_2CH_2OCH_3$ and are free from amino, nitro, chloride and fluoride groups.

10. A pharmaceutical preparation for treating tumors in a host which comprises a tumor-treating effective amount of one or more titanocene derivatives comprising two cyclopentadiene rings linked to titanium as a central atom, which are bound covalently to two phenoxy groups which possess a radical substituent R selected from the group consisting of H, $COOCH_3$, $COOCH_2H_5$, and $COOCH_2CH_2OCH_2CH_2OCH_3$ and are free from amino, nitro, chloride and fluoride groups.

11. The preparation of claim 10 which also contains other pharmaceutically active ingredients.

* * * * *